United States Patent [19]

Matteucci

[11] Patent Number: 5,264,562
[45] Date of Patent: Nov. 23, 1993

[54] OLIGONUCLEOTIDE ANALOGS WITH NOVEL LINKAGES

[75] Inventor: Mark Matteucci, Burlingame, Calif.

[73] Assignee: Gilead Sciences, Inc., Foster City, Calif.

[21] Appl. No.: 690,786

[22] Filed: Apr. 24, 1991

Related U.S. Application Data

[63] Continuation-in-part of Ser. No. 559,957, Jul. 30, 1990, which is a continuation-in-part of Ser. No. 558,882, Jul. 27, 1990, abandoned, which is a continuation-in-part of Ser. No. 448,941, Dec. 11, 1989, abandoned, which is a continuation-in-part of Ser. No. 426,286, Oct. 24, 1989, abandoned.

[51] Int. Cl.$^5$ .................. C07H 19/00; C07H 21/00
[52] U.S. Cl. .................. 536/23.1; 536/25.3
[58] Field of Search ............ 536/27, 28, 29, 23.1, 536/25.3; 514/44

[56] References Cited

U.S. PATENT DOCUMENTS 4,458,066 7/1984 Caruthers et al. ............ 536/25.34

FOREIGN PATENT DOCUMENTS 8905853 6/1990 PCT Int'l Appl. .

OTHER PUBLICATIONS

Agarwal et al., *Nucleic Acids Res.* (1979) 6:3009–3024.
Agarwal et al., *Proc. Natl. Acad. Sci.* (1988) 86:7079–7083.
Miller et al., *Biochemistry* (1981) 20:1874–1880.
Marcus-Secura et al., *Nucleic Acids Res.* (1987) 15:5749–5763.
Jayaraman et al., *Proc. Natl. Acad. Sci.* (1981) 78:1537 1541.
Coull et al., *Tetrahedron Letters* (1987) 52:4202–4206.
Stirchak et al., *J. Organ. Chem.* (1987) 52:4202–4206.
Cosstick et al., *Tetrahedron Letters* (1989) 30:4693–4696.
van der Krol et al., *Biotechniques* (1988) 6(10):958–976.
Stein et al., *Cancer Res.* (1988) 48:2659–2668.
Mertes, M. P., and Coats, E. A., *J. Med. Chem.* (1969) 12(1):154–157.
Tittensor, J. R., *J. Chem. Soc.* (*Section C: Organic Chemistry*) (1971) 15:2656–2662.
Sekine, M., and Nakanishi, T., *J. Org. Chem.* (1989) 54:5998–6000.
Samukov, V. V., and Ofitsrov, V. I., *Chem. Abstracts* (1983) 98:547 (abstract No. 161094x).
Veeneman, G. H., et al., *Chem. Abstracts* (1991) 114:699 (abstract No. 7074h).

*Primary Examiner*—Johnnie R. Brown
*Assistant Examiner*—J. Oliver Wilson
*Attorney, Agent, or Firm*—Morrison & Foerster

[57] ABSTRACT

Oligonucleotide analogs wherein one or more phosphodiester linkages between adjacent nucleotides are replaced by an formacetal/ketal type linkage are resistant to nucleases and do not need to exhibit the diastereomerism characteristic of many other oligonucleotide analogs, and thus are capable of strong hybridization to target RNA or DNA. These oligonucleotide analogs are useful in therapies which modulate gene expression using "antisense" or other specifically binding oligomers.

12 Claims, 1 Drawing Sheet

FIG. 1

OLIGONUCLEOTIDE ANALOGS WITH NOVEL LINKAGES

CROSS-REFERENCE TO RELATED APPLICATION

This a continuation-in-part of U.S. Ser. No. 07/559,957 filed Jul. 30, 1990, now pending, which is a continuation-in-part of U.S. Ser. No. 558,882 filed Jul. 27, 1990, now abandoned, which is a continuation-in-part of U.S. Ser. No. 448,941 filed Dec. 11, 1989, now abandoned, which is a continuation-in-part of U.S. Ser. No. 426,286 filed Oct. 24, 1989, now abandoned. The disclosures of all of these applications are incorporated herein by reference in their entirety.

TECHNICAL FIELD

The invention relates to the construction of modified oligonucleotides and their components which are resistant to nucleases, have enhanced ability to penetrate cells, and are capable of binding target oligonucleotide sequences in vitro and in vivo. The modified oligonucleotides of the invention are particularly useful in therapies utilizing antisense DNAs to interrupt protein synthesis or otherwise inactivate oligonucleotides. More specifically, the invention concerns oligomers which contain at least one replacement of the phosphodiester linkage with a formacetal/ketal type linkage bearing sufficiently stabilizing electron withdrawing groups.

BACKGROUND ART

A rational basis for the development of oligonucleotide-based therapies for diseases whose etiology is characterized by, or associated with, specific DNA or RNA sequences has been recognized for a number of years. The basic principle is straightforward enough. The ultimate therapeutic agent, whether directly administered or generated in situ, is an oligomer which will be complementary to a DNA or RNA needed for the progress of the disease or will otherwise interact with it specifically as, for example, through triplex formation. By specifically binding to this target DNA or RNA, the ordinary function of these materials is interdicted.

The logic behind this approach is readily seen in visualizing the administration of, for example, an oligomer having a base sequence complementary to that of an mRNA which encodes a protein necessary for the progress of the disease. By hybridizing specifically to this RNA, the synthesis of the protein will be interrupted. It is also possible to bind even double-stranded DNA using an appropriate oligomer capable of effecting the formation of a specific triple helix by inserting the administered oligomer into the major groove of the double-helical DNA. The elucidation of the sequences which form the targets for the therapeutics is, of course, a problem which is specific to each target condition or disease. While the general principles are well understood and established, there remains a good deal of preliminary sequence information required for the design of a particular oligomeric probe.

One feature of the oligomeric probes which is, however, common to most targets is the structuring of the backbone of the administered oligomer so that it is resistant to endogenous nucleases and is stable in vivo, but also retains its ability to hybridize to the target DNA or RNA. (Agarwal, K. L. et al., *Nucleic Acids Res* (1979) 6:3009; Agarwal, S. et al., *Proc Natl Acad Sci U.S.A.* (1988) 85:7079.) As nucleases attack the phosphodiester linkage, a number of modified oligonucleotides have been constructed which contain alternate linkages. Among these have been methylphosphonates (wherein one of the phosphorous-linked oxygens has been replaced by methyl) phosphorothioates (wherein sulphur replaces one of these oxygens) and various amidates (wherein $NH_2$ or an organic amine derivative, such as morpholidates or piperazidates, replace an oxygen). These substitutions confer enhanced stability, for the most part, but suffer from the drawback that they result in a chiral phosphorous in the linkage, thus leading to the formation of $2^n$ diastereomers where n is the number of modified diester linkages in the oligomer. The presence of these multiple diastereomers considerably weakens the capability to hybridize to target sequences. Some of these substitutions also retain the ability to support a negative charge; the presence of charged groups decreases the ability of the compounds to penetrate cell membranes. (Miller, P. S. et al., *Biochemistry* (1981) 20:1874; Marcus-Secura, C. J. et al., *Nucleic Acids Res* (1987) 15:5749; Jayaraman, K. et al., *Proc Natl Acad Sci U.S.A.* (1981) 78:1537.) There are numerous other disadvantages associated with these modified linkages, depending on the precise nature of the linkage.

It has also been suggested to use carbonate diesters; however, these are highly unstable, and the carbonate diester link does not maintain a tetrahedral configuration exhibited by the phosphorous in the phosphodiester. Similarly, carbamate linkages, while achiral, confer trigonal symmetry and it has been shown that poly dT having this linkage does not hybridize strongly with poly dA (Coull, J. M., et al., *Tet Lett* (1987) 28:745; Stirchak, E. P., et al., *J Org Chem* (1987) 52:4202.

Of relevance to the present invention are modified phosphodiester linkages involving sulfur, rather than oxygen as a linking substituent. See, for example, Cosstick, R., et al., *Tet Lett* (1989) 30:4693-4696, which describes oligonucleotides containing 3'-thiothymidine.

The general approach to constructing oligomers useful in oligonucleotide therapy has been reviewed, for example, by van der Krol, A. R., et al., *Biotechniques* (1988) 6:958-976, and by Stein, C. A. et al., *Cancer Res* (1988) 48:2659-2668. The present invention provides an oligomeric linkage which is isosteric to the phosphodiester found in the native molecule, but which is resistant to nuclease digestion, and which is stable under physiological conditions, and which can be neutral so as to enhance cell permeation. Furthermore, the linkages can be achiral and thus do not lead to the problem of multiple diastereomers in the resulting compounds.

DISCLOSURE OF THE INVENTION

The invention is directed to modified oligonucleotides, including dimers and trimers, wherein the modification comprises replacing at least one phosphodiester linkage of the oligonucleotide with a formacetal/ketal type linkage of the formula $YCX_2Y$ wherein each Y is, independently, O or S. Although each X can be chosen independently, it is preferred that both X are identical so that the carbon is achiral. In order to provide adequate stability, X should be a substituent which is stabilizing to the linkage, as opposed to, for example, the conventional electron donating substituents. The requirements for X differ depending on the nature of each Y, as is further explained below.

In one aspect, the invention is directed to oligonucleotides and intermediates in their synthesis which contain, in place of at least one phosphodiester or other conventional linkage, a linkage of the formula —YCX$_2$Y— wherein each Y is independently O or S and wherein each X attached to the same carbon is independently chosen, but preferably both X are identical. X provides sufficient electron withdrawal to stabilize the linkage, as required by the formacetal/ketal linkage —OCX$_2$O—, the mixed linkages —SCX$_2$O— and —OCX$_2$S— or the dithio analog —SCX$_2$S—. Stated another way, the invention is directed to compounds of the formula Formula 1 and their derivatized forms, as defined below, wherein each B is independently a purine or pyrimidine residue or their analogous forms, as defined below, wherein each Y is independently O or S, and wherein each Z is independently or is a conventional phosphodiester substitute (including but not limited to —P(O)S—, —P(O)NR$_2$—, —P(O)R—, or P(O)OR'—; —CO— or —CNR$_2$— wherein R is H or alkyl (1–6C) and R, is alkyl (1–6C)), wherein X is as above defined, and each m is independently 0 or 1, n is 1–200.

At least one Z must be CX$_2$. In additional aspects, the invention is directed to intermediates in the synthesis of the compounds of the invention and to compositions for and methods to use these compounds in therapies which rely on specific binding to target oligonucleotides ("antisense" therapies).

MODES OF CARRYING OUT THE INVENTION

A. Definitions

As used herein, "antisense" therapy refers to administration or in situ generation of DNA or RNA oligomers or their derivatives which bind specifically to a target nucleic acid sequence. The binding may be by conventional base pair complementarity, or, for example, in the case of binding to DNA duplexes, through specific interactions in the major groove of the double helix. In general, "antisense" refers to the range of techniques generally employed under this description in the art, and includes any therapy which relies on specific binding to oligonucleotide sequences.

"Oligomers" or "oligonucleotides" includes sequences of more than one nucleotide and specifically includes short sequences such as dimers and trimers.

"Derivatives" of the oligomers include those conventionally recognized in the art. For instance, the oligonucleotides may be covalently linked to various moieties such as intercalators, substances which interact specifically with the minor groove of the DNA double helix and other arbitrarily chosen conjugates, such as labels (radioactive, fluorescent, enzyme, etc.). These additional moieties may be (but need not be) derivatized through the formacetal/ketal type linkage as part of the linkage itself. For example, intercalators, such as acridine can be linked through an —Y—CH$_2$—Y— attached through any available —OH or —SH, e.g., at the terminal 5' position of RNA or DNA, the 2' positions of RNA, or an OH or SH engineered into the 5 position of pyrimidines, e.g., instead of the 5 methyl of cytosine, a derivatized form which contains —CH$_2$CH$_2$CH$_2$OH or —CH$_2$CH$_2$CH$_2$SH in the 5 position. A wide variety of substituents can be attached, including those bound through conventional linkages. Accordingly the indicated —OH moieties in the oligomer of formula (1) may be replaced by phosphonate groups, protected by standard protecting groups, or activated to prepare additional linkages to other nucleotides, or may be bound to the conjugated substituent. The 5' terminal OH is conventionally phosphorylated; the 2'-OH or OH substituents at the 3' terminus may also be phosphorylated. The hydroxyls may also be derivatized to standard protecting groups. In addition, specifically included are the 2'-derivatized forms of the nucleotide residues disclosed in copending U.S. Ser. No. 07/425,857 filed on even date herewith, assigned to the same assignee, and incorporated herein by reference. The phosphodiester linkage shown may be replaced by alternative linking groups as long as one linkage is of the form —YCX$_2$Y—. These alternative linking groups include, but are not limited to embodiments wherein "Z" is P(O)S, P(O)NR$_2$, P(O)R, P(O)OR', CO, or CNR$_2$, wherein R is H or alkyl (1–6C) and R' is alkyl (1–6C). Not all Z in the same oligomer need to be identical.

"Analogous" forms of purines and pyrimidines are those generally known in the art, many of which are used as chemotherapeutic agents. An exemplary but not exhaustive list includes 4-acetal cytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'methoxycarbonylmethyluracil, 5-methoxyuracil, 2-methylthio-N6-isopentenyladenine, uracil-5-oxyacetic acid methylester, uracil-5-oxyacetic acid, wybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine. A particularly preferred analog is 5-methylcytosine.

The invention is directed to new compounds which are useful in antisense-based therapy and intermediates in their production, as well to methods to synthesize these compounds and their intermediates. In general, the invention compounds show enhanced stability with respect to nucleases by virtue of their modified linkages, as well as enhanced ability to permeate cells. Desirably, multiple phosphodiester linkages in the unmodified oligonucleotides are substituted by corresponding formacetal/ketal linkages or their thio-containing analogs. Though it is preferred that these substituent linkages be non-chiral in nature to enhance the ability to hybridize, useful compounds of the invention include those where each X is chosen independently. Thus chiral forms may also be used, and where multiple formacetal/ketal or analogous thio-linked linkages occur in the oligonucleotide, a number of embodiments of X— may be included.

As stated above, the linking moiety —YCX$_2$Y—, may be a formacetal/ketal or one or both of the oxygens may be replaced by a sulfur. The replacement of one or both oxygens by a thiol linkage may be advantageous in that the length of the carbon-sulfur bond corresponds more closely to the length of the phosphorus-oxygen bond in the native oligonucleotide. Furthermore, greater scope is possible in connection with the substituent X groups as further described below, since the thio analogs are more stable to hydrolysis, especially under acidic conditions. In addition, the preparation reactions may proceed more smoothly due to the enhanced nucleophilicity of the SH group in the intermediates.

For ease in representation, the structure of the "wild type" oligonucleotides (and their derivatives as defined above) will sometimes be shown in the following shorthand form:

In this representation, B represents the usual purine or pyrimidine bases such as A, T, C, G as well as any modified forms of these bases that might be desirable in a particular therapeutic or compound. It is also understood that for some particular applications, one or more of these "B" groups may be replaced by any arbitrary substituent so long as that substituent does not interfere with the desired behavior of the oligomer. In most cases, these may be replaced by analogous substituents as defined above.

The corresponding shorthand for the modified oligomers of the invention is, similarly, where similar remarks apply to the nature of B and to the possibility of derivatization. In addition, as the linkages of the invention are stable to nuclease attack, in addition to modified forms of DNA, similarly modified forms of RNA are included in the invention.

It should be clear that the invention compounds are not limited to oligomers of homogeneous linkage type, and that alternating or randomly distributed phosphodi-ester (or other substituted) and formacetal/ketal type linkages are contemplated. Since the oligomers of the invention can be synthesized one nucleotide residue at a time, each individual linkage, and the nature of each individual "B" substituent can be chosen at will. However, for most applications, it is contemplated that major portions of the oligomer designed for therapeutic use would contain the formacetal/ketal type replacement linkage so as to minimize those portions of the molecules subject to attack by nucleases and to enhance cell permeation.

X must be of such a nature so as to be stabilizing of the substitute invention link. For embodiments wherein both Y are O— i.e. —OCX$_2$O—; alkyl substituents are unworkable unless one X attached to the ketal C is compensated by a high electron withdrawing ability of the other. A preferred embodiment for X in this case is simply H—; this has sufficient electron-withdrawing characteristics to result in adequate stability. Other preferred embodiments of X include carboxyl or the esters or amides thereof; halide, including F, Cl, Br and I; NO$_2$; phosphate or phosphorate at low pH; —SOR or —SO$_2$R wherein R' is an organic residue, typically alkyl (1-6C); or is —CN or —CF$_3$. Other embodiments include electron withdrawing groups separated from the linking C of —OCX$_2$O— by 1-3 methylene groups; i.e., X is —(CH$_2$)$_n$W wherein n is 1-3 and W an electron withdrawing substituent. In general, the greater the value of n, the more electron withdrawing W must be. Typical embodiments of W include primary, secondary, or tertiary amines, or W heteroatom, such as hydroxymethyl, or substituted hydroxymethyl, such as OCH$_2$OCH$_2$OH, or e.g., OCH$_2$CH$_2$OH. In addition, both X together may constitute a cyclic substituent containing at least one heteroatom. In these embodiments, the ketal linkage may thus be, for example, Suitable X substituents include, therefore, —H, F, —Cl, —Br, —NO$_2$, —SCH$_2$CH$_3$, —COOH, —COOCH$_3$, —COOCH(CH$_3$)$_2$, —CONHCH$_3$, —CH$_2$F, —CF$_3$, —CH$_2$COOCH$_3$, —CH$_2$CONHCH$_2$CH$_3$, —CH$_2$CH$_2$COOH, —CH$_2$CH$_2$NH$_2$, —CH$_2$CH$_2$NHCH$_2$CH$_3$, —CH$_2$CH$_2$CF$_3$, and so forth. If the Xs attached to the ketal linkage are different, both Xs together must confer sufficient electron withdrawing ability to stabilize the oligomer.

Particularly preferred are embodiments wherein both X are H or F or where both X taken together are —(CH$_2$)$_2$O(CH$_2$)$_2$.

Formacetal/ketal type linkages wherein one or more of the linking oxygens is replaced by a sulfur are inherently more stable than their oxygen containing analogs. Thus, linkages of the formula —OCX$_2$S—, —SCX$_2$O—, and —SCX$_2$S—, are less demanding of electron withdrawal than the linkage —OCX$_2$O—. Accordingly, all of the embodiments set forth above for X in the context of the formacetal/ketal linkage are suitable, but in addition, X may also be alkyl, in general, lower alkyl (1-4C) or even phenyl, so long as the phenyl contains an electron withdrawing substituent in the appropriate position—e.g. 2-nitro, 4-nitro or 2,4-nitrophenyl. Of course, the linkage —SCX$_2$S— is the most tolerant of electron donation. The extent to which the spectrum of substituents for X can be extended into those which are potentially electron donating can readily be determined by simple assays of stability of the resulting product, and this determination, and a good deal of predictability of the tolerance of these linkages, is within the ordinary skill of the art. However, embodiments wherein both X and H are preferred.

It should further be noted that if X, itself, contains a functional group, X can be used to tether desired moieties useful as adjuncts in therapy, for example, intercalators or minor groove reactive materials, such as netropsin and its derivatives, anthramycin, quinoxaline antibiotics, actinomycin, and pyrrolo (1-4) benzodiazepine derivatives.

The oligomers of the invention may contain an arbitrary member of the formacetal/ketal type linkages of the invention. These may be identical to each other or different by virtue of the embodiments chosen for X, and/or by virtue of the choice of —OCX$_2$O—, —SCX$_2$O—, —OCX$_2$S— or —SCX$_2$S—. Since the oligomers are prepared sequentially, any pattern of linkage types, base substituents, and saccharide residues may be used.

In some preferred embodiments, the formacetal/ketal type linkages alternate in a regular pattern. Preferred embodiments include oligomers which contain, for example, a series of 3-8, formacetal type linkages alternating regularly with respect to regions of diester linkages. Particularly preferred are alternating structures wherein a formacetal type linkage is followed by a phosphodiester followed by a formacetal followed by a phosphodiester, etc., so that there is a one-by-one alternation of the two types of linkages. Additional alternatives might include, for example, a formacetal type linkage followed by two diesters followed by a single formacetal type linkage followed by two diesters, etc. A variety of regularly variant patterns is readily derived.

It is also clear that arbitrary modifications may be made to one or more of these saccharide residues; however, for the most part, the standard 3'-5, nucleotide linkage between ribosyl residues is most convenient. Where this is the case, further abbreviation of the structures may be used. For example, in standard DNA (or RNA) the sequences are generally denoted by the sequence of bases alone, such as, for example, ATG CGC TGA. In general, it is simply stated in advance whether this represents an RNA or DNA sequence. In the compounds of the invention, similar notation will be used for modifications of otherwise physiological DNA or RNA molecules but the phosphodiester linkages replaced by the formacetal/ketal type will be noted in the structure. Thus, 5'-ATG (OCX$_2$O) GTCA (SCX$_2$O) AGG-3' indicates an oligonucleotide ATGGTCAAGG with two of the phosphodiester linkages modified in the noted positions.

The modified oligomers of the invention are, as stated above, useful in applications in antisense therapy. The specific targets of such therapies include: viral diseases, malignant cell growth, bacterial diseases, and, in fact, any condition associated with the presence of a characteristic DNA or RNA or products thereof. The compounds of the invention can be applied in the same manner as alternative modified oligonucleotide analogs, and the manner of such application is conventional in the art.

B. Utility and Administration

Accordingly, the modified oligomers of the invention are useful in therapeutic, diagnostic and research contexts. In therapeutic applications, the oligomers are utilized in a manner appropriate for antisense therapy in general—as described above, antisense therapy as used herein includes targeting a specific DNA or RNA sequence through complementarity or through any other specific binding means, for example, sequence-specific orientation in the major groove of the DNA double-helix, or any other specific binding mode. For such therapy, the oligomers of the invention can be formulated for a variety of modes of administration, including systemic and topical or localized administration. Techniques and formulations generally may be found in *Remington's Pharmaceutical Sciences*, Meade Publishing Co., Easton, Pa., latest edition.

For systemic administration, injection is preferred, including intramuscular, intravenous, intraperitoneal, and subcutaneous. For injection, the oligomers of the invention are formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays, for example, or using suppositories. For oral administration, the oligomers are formulated into conventional oral administration forms such as capsules, tablets, and tonics.

For topical administration, the oligomers of the invention are formulated into ointments, salves, gels, or creams, as is generally known in the art.

In addition to use in therapy, the oligomers of the invention may be used as diagnostic reagents to detect the presence or absence of the target DNA or RNA sequences to which they specifically bind. Such diagnostic tests are conducted by hybridization through base complementarity or triple helix formation which is then detected by conventional means. For example, the oligomers may be labeled using radioactive, fluorescent, or chromogenic labels and the presence of label bound to solid support detected. Alternatively, the presence of a double or triple helix may be detected by antibodies which specifically recognize these forms. Means for conducting assays using such oligomers as probes are generally known.

In addition to the foregoing uses, the ability of the oligomers to inhibit gene expression can be verified in in vitro systems by measuring the levels of expression in recombinant systems.

It may be commented that the mechanism by which the specifically-binding oligomers of the invention interfere with or inhibit the activity of a target RNA or DNA is not always established, and is not a part of the invention. If the oligomer seeks, for example, a target mRNA, translation may be inhibited. In addition, by binding the target, the degradation of the mRNA message may be enhanced, or the further processing of the RNA may be inhibited. By formation of a triple helix, the transcription or replication of the subject DNA may be inhibited; furthermore, reverse transcription of infectious RNA or replication of infectious DNA is interfered with. It is also thought that the immune function may be modulated through physiological mechanisms similar to those induced by double-stranded RNA as exemplified by the "ampligen" system or similar to those used to suppress systemic lupus erythematosus. It is also possible to design oligomers that bind to arbitrary target molecules, such as proteins; these sequences can be obtained using techniques such as those disclosed in U.S. application Ser. No. 586,769, filed Sep. 21, 1990, the relevant portions of which are incorporated herein by reference. The oligomers of the invention are characterized by their ability to target specific substances, including proteins and oligonucleotides regardless of the mechanisms of targeting or the mechanism of the effect thereof.

Finally, it is understood that the DNA can be derivatized to a variety of moieties which include, intercalators, chelators, lipophilic groups, label, or any other substituent which modifies but does not materially destroy the oligomeric character of the backbone.

C. Synthesis of the Analogs

Schemes 1–4 show structural formulas as traditionally drawn. In schemes 5–7, notation is substituted wherein the indicated nucleoside is designated by the corresponding starred base. Thus, the starting materials in Reaction Scheme 1 would be shown as 5'DMTO-T*-OH-3' and 5'HO-T -OSiMe$_2$Tx 3' and the product of step 3 as 5'HO-T*-OCH$_2$O-T*-OSiMe$_2$Tx 3'. Generally, the single reactants are represented 5' PrO-B*-OPr 3' and the products are represented 5' PrO-B*-YCX$_2$Y-B*-OPr 3' wherein B* represents a nucleoside residue, Y and X are as above-defined, and each Pr is independently H, a protecting group, or a phosphate/phosphite group.

Schemes 1–7 show illustrative procedures for preparing the oligonucleotides of the invention containing formacetal/ketal linkages. The thymidyl derivatives are used as illustrations.

In one general approach, the oligomers (including dimers and trimers) of the invention which contain substituted formacetal/ketal linkages are coupled using a modification of the disaccharide synthesis method of Nicolaou, K. C., et al. *J Am Chem Soc* (1983) 105:2430. The sugar derivatized monosaccharides to be coupled are protected in the positions where participation in the linkage is not desired; one partner is treated with a reagent to form a thioacetal intermediate, such as ClCX$_2$SMe in the presence of a base and in an inert solvent to obtain the methyl thioacetal derivative at the free hydroxyl. This activated sugar is then reacted with the saccharide to which it is to be coupled, said saccharide protected at all positions other than the hydroxyl (or sulfhydryl) intended to form the linkage. This reaction is conducted in the presence of N-bromosuccinimide and a sterically hindered weak base to obtain the protected dimer. The resulting suitably deprotected dimer can then be extended by repeating this conjugation. The use of this general approach to the formation of a formacetal linked trimer is shown in Reaction Scheme 1.

Reaction Scheme 1

Reaction Scheme 1

-continued

In step 1, thymidine protected at the 5, position with dimethoxytrityl (DMT) is converted to the methyl thioacetal or other thioacetal. The ClCH$_2$SCH$_3$ reagent shown may be replaced by the corresponding bromide, or other thioethers of the general formula ClCX$_2$SR or BrCX$_2$SR. The reaction in step 2 is conducted in the presence of N-bromosuccinimide (NBS) and 2,6-di-t-butylpyridine (2,6 DTBP) in methylene chloride for reaction of the thioacetal with a 5' hydroxyl of thymidine protected at the 3' position with thexyl dimethylsilyl. It should be noted that the hindered pyridine, 2,6-t-butylpyridine is required in step 2 since the less hindered dimethyl form is alkylated by the activated acetal. This results in the protected dimer containing the desired formacetal/ketal linkage. Deprotection in acid liberates the 5' position from the protecting trityl group, providing a dimer which can then be reacted with the 5'-DMT-3'- methylthioacetal as in step 2 in an additional step 4 to obtain the protected trimer, which can be deprotected as in step 3 in an additional step 5.

These steps can be repeated choosing any derivatized sugar for the 5'-protected 3'-derivatized reagent in a reaction analogous to step 2 to obtain oligomers of any desired length.

In a modified form of the scheme shown in Reaction Scheme 1, improved yields are obtained by utilizing, instead of NBS and 2,6 DTBP, treatment with bromine in the presence of 2,6-diethylpyridine and molecular sieves, followed by treatment by tetrabutyl ammonium fluoride in a tetrahydrofuran (THF) solvent. In this alternative approach, the dimer deprotected in the 3' position is obtained, although the DMTO protection at the 5' position is retained. In general, the 5' DMTO-T*-OCH$_2$SCH$_2$ monomer is mixed with a slight excess of the 5'HO-T*-OSiMe$_2$Tx monomer in slight excess and is further mixed with 2,6-diethylpyridine in an inert solution. This is followed by the addition of dissolved bromine and the mixture is stirred for several hours at room temperature. After extraction with mild base, the organic fraction is redissolved in aprotic polar solvent and treated with a solution of tetrabutyl ammonium fluoride at room temperature for 10 minutes-about 1 hour. The condensed dimer is recovered by extraction into an organic solvent from base and purified using conventional means.

Reaction Schemes 2, 3 and 4 show the production of dimers and trimers which have linkages of the form 3'-OCX$_2$S-5'. Reaction Schemes 2 and 3 show the preparation of the individual components of the dimer, Reaction Scheme 4 the dimer formation. Thymidine derivatives are also used in this example.

Reaction Scheme 2

Reaction Scheme 2 describes the preparation of the 3'-protected thymidine having SH in the 5' position As shown in the sequence of reactions, a 5' dimethoxytrityl thymidine is silylated using thexyl dimethylsilyl chloride. The resulting 3'-silylated sugar is hydrolyzed in 80% acetic acid and the 5'-hydroxy is then activated using p-tolylsulfonyl chloride in pyridine; the p-tolylsulfonyl group is then replaced using a salt of thioacetic acid as described by Reist, E., et al., *J Am Chem Soc* (1964) 29:554. The acetalthioester can be stored, and is hydrolyzed immediately prior to use to prevent disulfide formation, as described in the Reist paper.

Reaction Scheme 3 describes the activation of the 3'OH subsequent to conversion of the 540 position to a protected sulfhydryl, if desired. As shown, the 5'-dimethoxytrityl protected thymidine is alkylated with chloromethylthiomethane in THF using sodium hydride as a base and sodium iodide as a catalyst To obtain the 3'thioacetal other reagents besides chloromethylthiomethane may be used, such as chloromethylthiobenzene and chloromethyl-2-thiopyridine, or the corresponding bromides of any of the above These may even be superior or lead to thioacetal products which have leaving groups superior to the methylthio shown. The protecting dimethoxytrityl group is then removed with 80% acetic acid, for example, and activated and converted to the thioester as was described in Reaction Scheme 2—activation with tosyl chloride, followed by treatment with a salt of thioacetic acid.

The acetal thioester may itself subsequently be used in the condensation reaction with the product of Reaction Scheme 2, but superior methods for protection of the SH are available. In one such scheme, the acetal/thio group is hydrolyzed and the resulting sulfhydryl reacted with dimethoxytrityl chloride or trimethoxytrityl chloride generating a trityl sulfide, according to the procedure of Hiskey, R. G. et al., *J. Org. Chem* (1966) 31:1188. Subsequent deprotection is effected under mild acid conditions. In a second approach, the hydrolyzed free SH group is reacted with dinitrophenol sulfonyl chloride, thus generating a disulfide group, according to the method of Fontana, A., *J Chem Soc Chem Commun* (1975) 976. The disulfide can be removed with reducing agents such as mercaptoethanol or sodium borohydride. Both of these alternative schemes of protection result in a visible color when deprotection is conducted.

The protected thioacetal monomer resulting from scheme 3 is then reacted with the 3' -protected 5' sulfhydryl product of Reaction Scheme 2 as shown in Reaction Scheme 4. The components are mixed in slightly less than an equivalent of N-bromosuccinimide in the presence of an excess of a hindered base, such as 2,6-di-t-butyl pyridine as shown. The NBS and 2,6-DTBP are first added to the blocked thioacetal and the activated 3' thioacetal thymidine is then reacted with the 5' SH thymidine. This order of addition is required to prevent the side reaction of the reagents with the 5'SH group. As for Reaction Scheme 1, improved yields are obtained by substituting treatment of the components with 2,6-diethyl pyridine and bromine ($Br_2$) for NBS and 2,6-DTBP. The resulting dimer can be extended as shown in Reaction Scheme 4, or as many times as desired by repeating the condensation reaction with another equivalent of the thioacetal.

The 3' thionucleosides are also available in the art, and can be synthesized as described by Zuckermann, R. et al., *Nucl Acids Res* (1985) 15:5305 and 3' thiothymidine has been used for the synthesis of oligonucleotides as described by Cosstick, R. et al. *Tet Lett* (1989) 30:4693-4696, cited above. The 3' thionucleosides can be converted to the dithio analogs of the acetals in a manner analogous to the first steps of Reaction Scheme 1 or Reaction Scheme 3 to provide a suitable leaving group for nucleophilic attack by either an SH or OH at the 5' position of the adjacent nucleoside, in a manner analogous to that shown in Reaction Scheme 1 or 4. Thus, in a manner analogous to the methods shown for the preparation of the formacetal/ketal and the linkage of the formula —OCX$_2$S—, dimers, trimers, and oligomers with linkages of the formulas —SCX$_2$O— and —SCX$_2$S— can be obtained.

A modified approach to obtaining the 5'—OCX$_2$S—3' (—SCX$_2$O—) linkages is shown in Reaction Scheme 5.

be activated at the 5' position and reacted with the 5' protected, 3' SH nucleoside.

Reaction Schemes 6 and 7 show the syntheses of linkages of the formulas —OCF$_2$O— and the corresponding linkage wherein X$_2$ comprises the residue of a dioxane ring.

In Reaction Scheme 6, advantage is taken of the reactivity of thiocarbonyl imidazole to activate a free 3'-OH group in a protected thymidine nucleoside. The activated nucleoside is then condensed with a 5'-OH, 3'-protected nucleoside to obtain the dimer linked through —OCSO—. The intermediate dimer is then desulfurized and fluorinated by treatment with diethylamino trifluoro sulfur (DAST) in the presence of acetonitrile

5' DMTO—T*—SCH$_2$O—T*—OH 3'

The starting material, 5'-methylthiomethyl-3'-t-butyldimethyl silylthymidine, is first prepared by reduction of 3'-t-butyldimethyl silylthymidine by a suitable hydride by reaction at room temperature followed by addition of sodium iodide and chloromethyl methyl sulfide. This reaction mixture is mixed for 1 hour at room temperature and diluted with an inert solvent and the activated, protected thymidine 5' MeSCH$_2$O-T*-OSiMe$_2$-Tx3'V purified.

To form the dimer, 5'DMTO-T*-SH 3' is mixed with an excess of 2,6-diethylpyridine in an inert solvent. To this solution, after stirring for a suitable period at room temperature, an approximately 1M solution of bromine in inert solvent is added. This solution is also stirred for about 30 minutes and the 5'-DMT-3'-thiothymidine, dissolved in an inert solvent, is then added.

The reaction mixture is held at room temperature for 1-3 hours, preferably around 2 hours and the reaction mixture is worked up to isolate the dimer product 5' DMTO-T*-SCH$_2$O-T*-OH 3'. The reaction can be repeated as desired to form trimers or higher oligomers by rederivatizing the 3' OH of the dimer to form the silylate and deprotecting and activating the 5' position of the dimer to obtain the methyl thiomethyl ether of the formula 5' MeSCH$_2$O-T*-SCH$_2$O-T*-OSiMe$_2$Tx 3'. This is then reacted with 5' DMTO-T*-SH 3' as set forth in Reaction Scheme 5. Alternatively, corresponding dimers prepared as in Reaction Schemes 1 or 4 may In more detail, the 5' protected thymidine is reacted with the thiocarbonylimidazole in the presence of acetonitrile under an inert atmosphere at elevated temperatures of about 60° C., for 12-24 hours, preferably about 16 hours or until reaction is complete. After cooling, the condensation product is recovered in an organic layer and treated with the 3' protected thymidine, again in the presence of acetonitrile, to obtain the —OCSO— linked dimer. The formation of dimer takes place under an inert gas in a sealed vessel at about 80° C. for about 48 hours. After dilution with inert solvent such as methylene chloride, the dimer is recovered and purified for example by column chromatography.

The purified material is then dried and desulfurized and fluorinated by treatment with DAST in the presence of dry acetonitrile under inert gas at about 40° C. for about 16 hours. The product containing the —OCF$_3$— linkage is then recovered Reaction Scheme 7 shows the synthesis of the dimer linked through a tetrahydropyran ketal In Reaction Scheme 7, as shown, Bz represents benzoyl, Pv represents pivaloyl, and TSA is toluene sulfonic acid.

Reaction Scheme 7

-continued
Reaction Scheme 7

As shown generally, the 3'-benzoylthymidine is reacted with 2,3-dihydro-4-methoxypyran to obtain the 5'-derivatized 3'-benzoylthymidine. The 5, position, derivatized to the 4-methoxytetrahydropyran-4-yl substituent, is then reacted with a 5'-protected thymidine to obtain the tetrahydropyran ketal. The condensation to form the dimer is conducted in the presence of molecular sieves under inert gas with stirring at about 20° C. for about 16 hours. After this period, p-toluenesulfonic acid (which has been dried) is added to the reaction mixture and the reaction is then agitated for about 2 more hours at about 50° C. under inert gas. The reaction is cooled to about 20° C. and quenched using triethylamine. The dimer, still protected at the 5' and 3'-positions is then purified using chromatographic methods. The steps of Reaction Scheme 7 can be repeated to obtain trimers or oligomers of any length, or the dimer may be used as a synthon for extensions with other nucleosides, dimers or oligomers.

For reaction schemes wherein the resultant retains the silyl protecting group, the resulting dimer, trimer or oligomer may be desilylated with tetrabutyl ammonium fluoride (TBAF) in an inert solvent such as THF and succinylated as a convenient linker for coupling to a solid support, such as controlled pore glass (CPG). The coupled modified oligomer can be used as a starting material for standard oligonucleotide synthesis, as, for example, using H-phosphonate chemistry as described by Froehler, B., et al., *Nucleic Acids Res* (1986) 14:5399. This synthesis involves deprotection of the 5, hydroxyl using dichloroacetic acid in methylene chloride and treatment with a 5' DMT-protected base 3' phosphonate in the presence of acetal chloride/pyrimidine/acetonitrile, and repetition of this deprotection and linkage protocol for any desired number of times.

Alternatively, the liberated 3-'OH can be linked via an ester linkage to a solid support analogous to standard oligonucleotide synthesis (Matteucci, M. et al., *J Am Chem Soc* (1981) 103:3185, for extension of oligonucleotide.

Additional formacetal/ketal type linkages can be inserted in the oligomer by phosphorylating the dimers, trimers, pentamers, etc., obtained as set forth in Reaction Schemes 1-7 and using these as the adducts in the oligomeric chain extensions. The final product is removed from the solid support by standard procedures, such as treatment with iodine in a basic aqueous medium containing THF or other inert solvent, followed by treatment with ammonium hydroxide. Deprotection of the nucleotide bases attached to the added nucleotides is also conducted by standard procedures.

The formacetal/ketal type linkage can be included at any arbitrary position in an oligonucleotide by substituting for a conventional monomer in the sequential synthesis, a protected dimer containing the formacetal/ketal type linkage which has been synthesized as in Reaction Schemes 1 and 4–7, by supplying the dimer as a suitably protected and phosphate-activated moiety. Thus either the 5' or 3' position of the dimer is provided with a protecting group and the other an activated form of phosphate/phosphite. The phosphate/phosphite is conveniently present as the triethylamine salt. This dimer is then incorporated at any desired location in the synthetic process using the standard steps of oligonucleotide synthesis.

Synthesis of the oligomer using standard techniques can be effected using the formacetal dimer synthons, for example, of the formula:

Formula A or generally of the formula 5' PrO-B\*-YCX$_2$Y-B\*-OPr, wherein one of Pr is a protecting group and the other is an activated phosphate/phosphite. Utilization of a series of these synthons results in the one-by-one alternation of the formacetal and phosphodiester linkages. Extended regions containing phosphodiester linkages are easily included by extending the chain with single nucleotides; extended regions containing the formacetal/ketal type linkages are obtained by extending the dimers in protocols analogous to those set forth in Reaction Scheme 1-7.

Any DNA synthesis chemistry such as phosphoramidate or phosphonate chemistry can be used to link monomers or dimers in a manner analogous to that set forth above.

The following examples are intended to illustrate but not to limit the invention:

EXAMPLE 1

Preparation of 5' TCTCCCTCTCTTT(OCH$_2$O)-T(OCH$_2$O)T-3'

See also: Matteucci, M. D., *Tet Lett* (1990) 31:2385.
Part A: Oligomer Preparation
Preparation of 5' Dimethoxytrityl 3'-Methylthiomethyl thymidine (Step 1):

Dimethoxytrityl thymidine (Peninsula Labs) (0.94 g) was rotovaped from pyridine two times and then from methylene chloride/toluene one time. The resulting foam was dissolved in 75 ml dry CH$_2$Cl$_2$ and 10 ml of dry THF. 10 mg of NaI and 0.21 g of NaH (60% dispersion in oil) was added under an argon atmosphere with stirring at 20° C. After 15 min the H$_2$ bubbling stopped and the reaction was stirred for another hour. Chloromethylthiomethane (158 ul) was added and stirring under argon continued for 16 hrs at 20° C. The reaction was quenched with 1M NaHCO$_3$, extracted and the organic layer dried with Na$_2$SO$_4$. The solution was then rotovaped to a foam and purified on a silica gel column using 5% isopropyl alcohol/CH$_2$Cl$_2$ as the eluent. Fractions were concentrated to a pure foam (yield 0.56 g) $^1$H NMR spectra was consistent with assigned structure.

Preparation of 3'Thexyldimethylsilyl thymidine:

Dimethoxytrityl thymidine (Peninsula Labs) (1 g), 20 ml of dry DMF, 193 mg of imidazole and 0.45 ml of thexyldimethylsilylchloride were combined under argon and stirred for 16 hr at 20° C. The reaction was then quenched with 2ml MeOH and rotovaped to a foam, dissolved in EtOH (20 ml) and treated with 0.6 ml of dichloroacetic acid for 16 hr at 20° C. The reaction was quenched with 1M NaHCO$_3$ and extracted with CH$_2$Cl$_2$. The organic layer was dried with Na$_2$SO$_4$. This solution was rotovaped to a foam, dissolved in 5 ml of diethylether and precipitated into 50 ml of hexane. The ether was rotovaped off as the white precipitate became heavy and upon filtration and drying, 0.5 g of pure white foam was recovered The $^1$H NMR spectra was consistent with the assigned structure.

Preparation of 5' OH 3' Thexyldimethylsilyl thymidine formacetal thymidine (Steps 2 and 3):

5' dimethoxytrityl 3' methylthiomethyl thymidine (78 mg) and 3' thexyldimethylsilyl thymidine (60 mg) were rotovaped from toluene and dissolved in 2 ml of dry toluene. 50 mg of activated 4A molecular sieves and Di-t-butyl pyridine (0.144 ml) were added and the reaction was stirred for 16 hr under argon. N-Bromosuccinimide (13 mg) was then added and the reaction stirred for 1 hr at 20° C. The reaction was quenched with 1M NaHCO$_3$ and extracted with CH$_2$Cl$_2$. The organic layer was dried with Na$_2$SO$_4$. The solution was rotovaped to a foam and then treated with 4 ml of 20% H$_2$O/HOAc for 2 hr at 20° C. The reaction was quenched in 1M NaHCO$_3$, extracted with CH$_2$Cl$_2$, dried with Na$_2$SO$_4$ and rotovaped to a foam. The foam was purified by silica gel chromatography using 3% to 10% IsOH/CH$_2$Cl$_2$ as the eluent yielding 60 mgs of pure product after evaporation of solvent. The $^1$H NMR spectra was consistent with the assigned structure.

Preparation of 5' Dimethoxytrityl 3' OH thymidine formacetal thymidine formacetal thymidine (Step 3):

5' OH 3' thexyldimethylsilyl thymidine formacetal thymidine (55 mg) was combined with dimethoxytrityl 3' methylthiomethyl thymidine (78 mg) and rotovaped from toluene. The resulting foam was dissolved in 2 ml of toluene/CH$_2$Cl$_2$ (1/1), 50 mg of activated 4A molecular sieves an di-t-butylpyridine (0.144 ml) were added and the reaction was stirred for 16 hr under argon. N-Bromosuccinimide (21 mg) was then added and the reaction stirred for 1 hr at 20° C. The reaction was quenched with 1M NaHCO$_3$ and extracted with CH$_2$Cl$_2$. The organic layer was dried from Na$_2$SO$_4$. The solution was rotovaped to a foam and treated with 1 ml of tetrabutylammonium fluoride in THF for 3 hr, extracted, dried and evaporated in normal fashion. The resulting foam was purified by preparative silica gel thin layer chromatography using a 10% IsOH/CH$_2$Cl$_2$ as the eluent The $^1$H NMR was consistent with the desired structure (yield 25 mg) A small aliquot (5 mg) was deprotected at the 5' end in normal fashion.

The resulting 5' OH 3' OH thymidine formacetal thymidine formacetal thymidine was used in further characterization. $^1$H NMR of this material in d$_6$ DMSO was consistent with the assigned structure. An aliquot of this was persilylated and a Fast Atom Bombardment Mass Spectrum was recorded. This confirmed the desired molecular weight Additionally the di OH material was used in the chemical and enzymatic stability studies previously mentioned.

Preparation of 5' Dimethoxytrityl 3' succinylate thymidine formacetal thymidine formacetal thymidine:

5' Dimethoxytrityl 3' OH thymidine formacetal thymidine formacetal thymidine (16 mg) was treated with 9 mg of succinic anhydride and a trace of dimethylamino pyridine in pyridine for 16 hr at 20° C. The reaction was then rotovaped and extracted with 30% BuOH/CH$_2$Cl$_2$ against H$_2$O. The organic layer was dried, rotovaped and purified on a silica gel column using 10% H$_2$O/CH$_3$CN as the eluent. Rotovaping yielded 15 mg of product.

Preparation of 5'-TCTCCCTCTCTTT(OCH$_2$O)T-(OCH$_2$O)T-3'

The 3' succinylated 5'-DMT thymidine formacetal thymidine formacetal thymidine from the previous paragraph was then bound to solid support and deprotected. Standard procedures were used to extend the oligomer to obtain the title compound.

Part B: Stability to Acid

The purified product of paragraph (A) above was treated with 20% water/formic acid at 80° C. for 1 hr, resulting in complete hydrolysis. However, when subjected to moderate acid treatment such as 1M HCl at 20° C. for 3 hrs or 20% water/acetic acid at 45° C. for 3 hrs, no hydrolysis was observed.

The title compound was also stable to snake venom phosphodiesterase under standard conditions for hydrolysis of phosphodiester bonds.

Part C: Hybridization to Complementary RNA

An RNA sequence complementary to the title compound was generated using T7 transcription Milligan, T. F., et al., *Nucleic Acids Res* (1987) 15:8783). This RNA was used to test the ability of the title compound to hybridize to its complement as compared to analogous sequences wherein the acetal linkages are replaced by phosphodiesters, phosphoramidates, or wherein the 3' terminal thymidyl nucleotides were deleted. The melting temperatures of complexes formed with the title compound and these controls were measured using 100 mM NaCl, 50 mM Tris, pH 7.5 under standard conditions as described by Summers, M. F., et al., *Nucleic Acids Res* (1986) 14:7421. The results are shown in Table 1, where "12mer" stands for the TCTCCCTCTCTT nucleotide sequence common to all of the samples. In the third oligomer, "W" represents the substituent —CH$_2$CH$_2$OMe in the amidate.

TABLE 1

|  | Tm |
| --- | --- |
| 12mer-T(OCH$_2$O)T(OCH$_2$O)T | 59.0 |
| 12mer-TTT | 59.5 |
| 12mer-T(PONHW)T(PONHW)T | 58.5 |
| 12mer | 56.5 |

As shown in Table 1, the three thymidines linked through formacetal linkages confer additional hybridization capability on the 12mer as compared to the 12mer alone. The additional hybridization is comparable to that conferred by extension by conventional phosphodiester linkages.

Part D: Binding to Duplex DNA

Using the footprinting method described in detail in Part C of Example 2 below, the formacetal-containing oligonucleotides of this example show ability to bind duplex DNA.

EXAMPLE 2

Preparation of 5'TCTC*(OCH$_2$O)TC*(OCH$_2$O)TC*(OCH$_2$O)TC-*(OCH$_2$OTTTT-3' or 5'TCTC*.-TC*.TC*.TTTT-3'

Part A: Preparation of Oligomers

A series of four oligomers as shown, wherein C* represents 5-methylcytosine and the dot between C* and T represents a linkage varied among the series of four oligomers was synthesized In the "phosphodiester" control oligomer, the dot represents a conventional phosphodiester linkage. In the "methylphosphonate" oligomer, the dot represents a methylphosphonate linkage. In the "methoxyethyl amidate" oligomer, the dot represents a methoxyethyl amidate linkage. In the "formacetal" oligomers of the invention, the dot represents a formacetal linkage as described herein and as shown above.

The phosphodiester oligomer was synthesized using the conventional techniques described by Froehler, B. C. et al., Nucleic Acids Res (1986) 14:5399. The remaining three oligomers were synthesized using this method, but with the incorporation of the appropriate dimer synthon. The methylphosphonate and the methoxyethyl amidate dimer synthons were constructed using 5'-DMT-N-benzoyl-5-methyldeoxycytidine and 3-t-butyldimethylsilyl thymidine as described, respectively, by Miller, P. S. et al., Biochemistry (1986) 25:5092, and by Froehler, B. C., Tet Lett (1986) 27:5575. The formacetal dimer synthon was prepared as described hereinabove and as reported by Mateucci, M. C. et al., Tet Lett (1990) 31:2385, cited above. The oligos resulting from the synthesis were deblocked with concentrated ammonia for 16 hours at 20° C. and gel purified using conventional techniques.

Part B: Hybridization to RNA Complement

The complementary RNA for use as a test compound was synthesized by T7 polymerase reaction on the appropriate primer template as described by Milligan, J. F. et al., Nucleic Acids Res (1987) 15:8783. Appropriate complementary DNA oligomers were also constructed.

The hybridization was tested using thermal denaturation comparisons in buffer containing salts designed to mimic intracellular salt composition and concentration—i.e., 140 mM KCl, 10 mM NaCl, 5 mM NaH$_2$PO$_4$, 5 mM MgCl$_2$, pH 7. UV absorption was measured in the temperature range 20° C.-80° C., and all oligomers gave monophasic transitions. Tm values were assigned by finding the temperature at which the slope of the curve was maximum.

These results are shown in Table 2.

TABLE 2

| Oligomer | $T_m$ ssRNA | $T_m$ ssDNA |
| --- | --- | --- |
| Phosphodiester | 60.0° C. | 49.5° C. |
| Methyl Phosphonate | 50.5 | |
| Methoxyethyl Amidate | 47.5 | 38.5 |
| Formacetal | 59.0 | 39.0 |

As shown in the table, the $T_m$ of the formacetal oligomer in comparison to the phosphodiester is roughly equal for single-stranded RNA. On the other hand, the $T_m$ values for the alternate analogs methylphosphonate and methoxyethyl amidate oligomers was appreciably lower. Thus, despite the advantages conferred by the formacetal linkage—for example, enhanced ability to cross cell membranes and enhanced nuclease resistance, no decrease in the hybridization power to single-stranded RNA was detected.

Part C: Binding to Duplex DNA

The "footprint" assay described by Cooney, M. et al., Science (1988) 241:456, was used. The assay is based on the ability of the oligomer bound to duplex to protect the duplex from digestion with DNAse I. Various concentrations of the test oligomer ranging from 0.1-10 μM were incubated with a P$^{32}$ radiolabeled restriction fragment bearing the target sequence at 1 nM concentration in 10 mM NaCl, 140 mM KCl, 1 mM MgCl$_2$, 1 mM spermine and 20 mM MOPS buffer at pH 7 for 2 hours. The target sequence for the set of oligomers prepared in Part A of this example was

—AGAGAGAGAGAAAA—
—TCTCTCTCTCTTTT—.

DNAse I was added to permit limited digestion, the samples were then denatured and subjected to polyacrylamide gel electrophoresis which separates the DNA fragments based on size.

Figure 1:
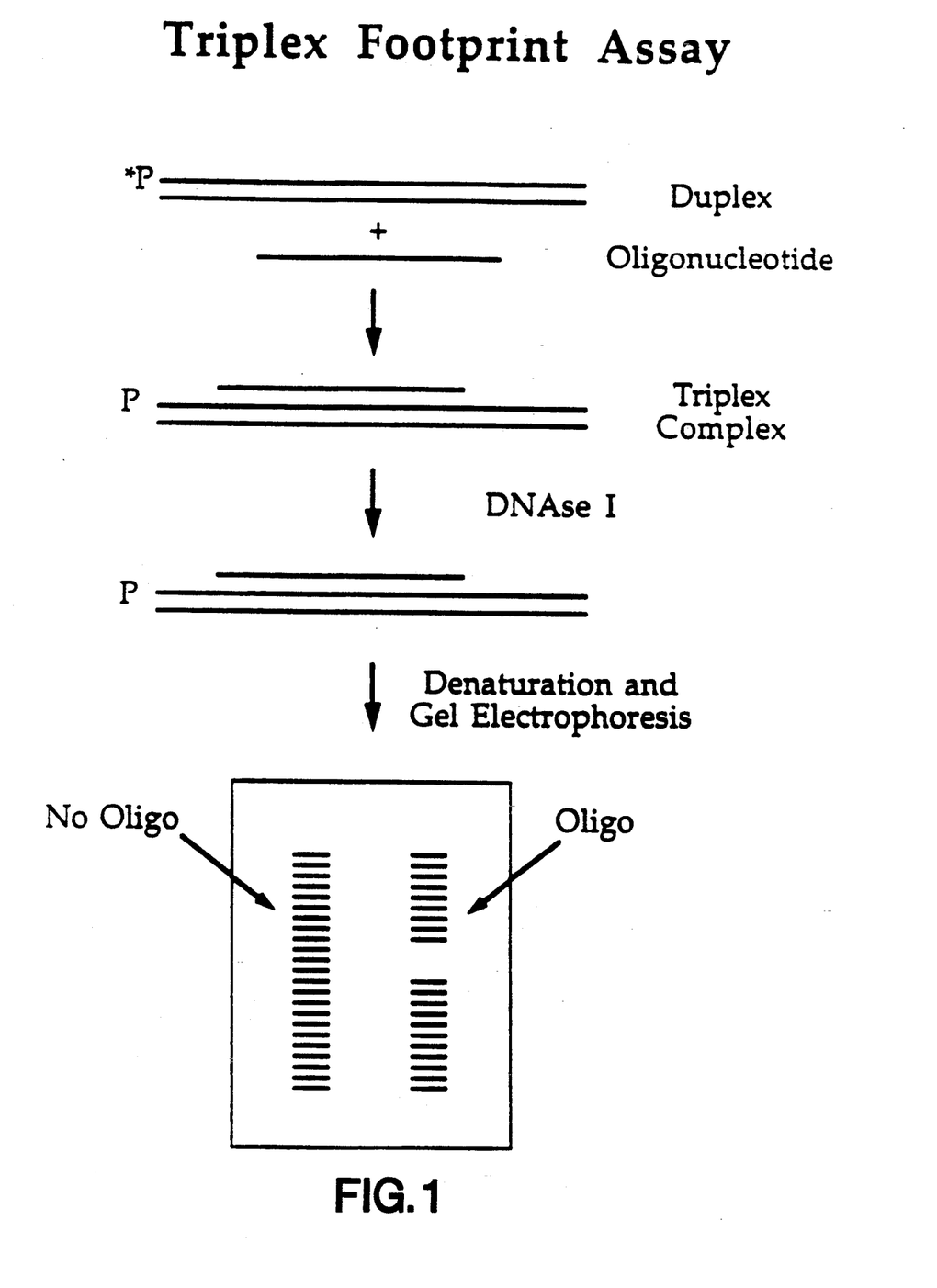
FIG. 1 shows an outline of, and idealized results of, the footprint assay for DNA-duplex binding.

An outline of the principle of the footprint assay and idealized results are shown in FIG. 1. As shown in FIG. 1, the labeled duplex, when treated with DNAse, should yield lengths of oligomer corresponding to cleavage at each diester linkage, thus obtaining the series of bands shown on the left in the idealized gel. On the other hand, when the duplex is protected by binding to the oligomer, the series of lengths represented by cleavage at the diester linkages in the region protected by binding to the oligomer is missing from the gel. This "footprint" indicates the region of protection. The results are semiquantitatively estimated by observing either the complete absence of, or only weak appearance of, bands in the region of the footprint.

The formacetal oligomer and the phosphodiester oligomer showed partial protection of the target sequence at 0.1 μM and more than 90% protection at 1 μM concentration of the oligomer. On the other hand, the methoxyethyl phosphoramidate and the methylphosphonate showed only partial protection at 1 μM and >90% protection at 10 μM. Thus, these oligomers appeared to have markedly less affinity for the duplex than the formacetal oligomer.

EXAMPLE 3

Preparation of 5'DMTO-T*-OCH$_2$O-T*-OH-3'

A mixture of 5'-DMTO-T*-OCH$_2$SCH$_3$, 3', prepared as in Example 1 (0.9 g, 1.5 mmol), 5'-HO-T*-OSiMe$_2$TX, also prepared as in Example 1 (0.8 g, 2.2 mmol), 2,6-diethylpyridine (1 g, 7.4 mmol) and molecular sieves (4A, 2 g) in dry benzene (60 ml) was stirred at room temperature (RT) for 1 hr. This was followed by addition of 1.5 ml of a 1.0M solution of bromine in benzene (1.5 mmol). The resulting solution was then stirred at RT for 2 hr and washed with saturated aqueous NaHCO$_3$ solution.

The organic solution was separated, dried (Na$_2$SO$_4$), evaporated to dryness, then redissolved in dry THF (10 ml) and treated with 4 ml of a 1.0M solution of tetrabutylammonium fluoride in THF at RT for 30 min. The reaction was concentrated and then partitioned between methylene chloride and saturated aqueous NaHCO$_3$ solution twice, dried, and evaporated to dryness. The residue was purified by flash column chromatography (silica gel) on a 25 mm column using one column volume of 1% TEA/CH$_2$CH$_2$, then two column volumes of 1% TEA/2.5% CH$_3$OH, and then one column volume of 1% TEA/5% CH$_3$OH/CH$_2$Cl$_2$. This afforded 0.84 g of product, 5' DMTO-T*-OCH$_2$O-T*-OH 3', as a colorless foam (71% yield).

EXAMPLE 4

Preparation and Characterization of 5' HO-T*-SCH$_2$O-T*-OH 3'

Part A: Preparation of the Dimer

To prepare 5'-methylthiomethyl-3'-t-butyldimethyl silyl thymidine, to a THF solution (15 ml) of 3'-t-butyl dimethyl silyl thymidine (1.8 g, 5 mmol) was added sodium hydride (0.24 g, 10 mmol). The solution was stirred at RT for 30 min; then sodium iodide (0.74 g, 5 mmol) and chloromethyl methyl sulfide (0.53 g, 5.5 mmol) were added. After 1 hr reaction at RT, the reaction mixture was diluted with methylene chloride (100 ml), then washed with saturated NaHCO$_3$ aqueous solution twice. The organic phase was isolated, dried over Na$_2$SO$_4$, concentrated to dryness, and purified by flash column chromatography on silica gel, affording 0.68 g of the 5' MeSCH$_2$O-T-O*SiMe$_2$tBu 3' (32% yield).

The 5' MeSCH$_2$O-T-O*SiMe$_2$tBu 3' from the preceding paragraph (0.55 g, 2.17 mmol), 2,6-diethylpyridine (1.46 g, 11 mmol), and molecular sieves (4 Å, 5 g) in dry benzene (40 ml) were stirred at RT for 30 min. This was followed by addition of 2.2 ml of a 1M solution of bromine in benzene (2.2 mmol). The resulting solution was stirred at RT for 30 min followed by addition of 5'-dimethoxytrityl-3'-thiothymidine (1.35 mmol) in benzene (20 ml). The 3'-thio sugar is prepared as set forth in Horwitz, P., et al., *J Org Chem* (1964) 29:2076, (Cosstick, R., et al., *Chem Soc Chem Commun* (1988) 992).

After 2 hr reaction at RT, the molecular sieves were filtered off, washed with benzene, and the combined benzene solution was washed with saturated NaHCO$_3$ aqueous solution, dried (Na$_2$SO$_4$), and concentrated to dryness. The residue was redissolved in THF (3 ml) and treated with 3 ml of a 1M THF solution of tetrabutylammonium fluoride at RT for 1 hr. The reaction mixture was concentrated, then partitioned between methylene chloride and saturated NaHCO$_3$ aqueous solution twice. The organic phase was separated, dried, and concentrated. The residue was purified by flash column chromatography on silica gel, affording 0.24 g of 5, DMTO-T*-SCH$_2$O-T*-OH 3' dimer (yield 22%).

Part B: Characterization of Oligonucleotides Containing —SCH$_2$O— Linkages

The TT 3'-thioformacetal thymidine dimer of the preceding paragraph was incorporated as a dimer block into the deoxyoligonucleotide sequence wherein tf is the 3' thioformacetal linkage, all other linkages are phosphodiester, Ċ is 5-methyl deoxycytidine and Q is an anthraquinone pseudonucleoside as described in U.S. Ser. No. 482,941, filed Feb. 20, 1990, and incorporated herein by reference. The ability of this oligomer to hybridize to RNA was assessed by thermal denaturation of the duplex of the oligomer and the RNA sequence 3' UAAAAGAAAGGAGGAAAAAU. Tm values for this denaturation were compared to those for identical sequences wherein either formacetal per se (—OCH$_2$O—) or phosphodiester was present in the "tf" position.

The Tm for the control phosphorodiester was 69° C.; the Tm for the formacetal was 67° C., and that for the 3' thioformacetal was 71° C.; thus, the 3' thioformacetal linkage hybridizes more strongly to RNA than either phosphodiester or the formacetal.

To assess triplex formation, thermal denaturation of the above oligomers and the duplex target 5' AAAA-GAAAGGAGGAAAAA was measured.

The Tm values for the triplex transitions at pH 6.2, (140 mM KCl, 5 mM NaCl, 5 mM MgCl$_2$, 5 mM Na phosphate) are: phosphodiester, 47.7° C.; formacetal, 44.1° C., 3' thioformacetal, 50.4° C. Thus, the 3' thioformacetal linkage confers stronger triplex formation than either the phosphorodiester or formacetal linkages.

Triplex formation was also assessed by DNAse I footprinting at pH 7.2, 20 mM MOPS, 140 mM KCl, 10 mM NaCl, 1 mM MgCl$_2$, 1 mM spermine. The 3' thioformacetal and exclusively phosphodiester oligomer were able to protect the target region from nuclease partially at 10 μM while the formacetal showed little protection at 100 μM.

EXAMPLE 5

Preparation of 5' HO-T*-OCF$_2$O-T*-OH

5' Pivaloyl-3'HO thymidine (1 g) and thiocarbonylimidazole (1.2 g) were combined in 8 ml of dry acetonitrile (CN) and heated under inert gas at 60° C. for 16 hr. TLC analysis showed complete conversion to a faster spot (5% isopropanol/CH$_2$Cl$_2$). The reaction was cooled, diluted with CH$_2$Cl$_2$ and washed with 1M HCl and then sodium phosphate buffer (pH 9). The organic layer was rotovaped to dryness, dissolved in dry ACN and rerotovaped; this was repeated three times This thiocarbonylimidazole product (746 mg) was combined with an excess of 5' HO-3'-isobutyl carbonyl-thymidine (810 mg) and 120 mg of tetrazole in 7 ml of dry ACN and 7 ml ethanol-free CHCl$_3$, heated under inert gas in a sealed vessel at 80° C. for 48 hr. The reaction was diluted with CH$_2$Cl$_2$, washed with phosphate buffer, concentrated and purified by flash column chromatography to yield one pure fraction of 145 mg and less pure fractions of 450 mg.

The pure material was then dried by coevaporation from dry ACN and desulfurized and fluorinated by treatment with 60 μl of diethylamino trifluoro sulfur (DAST) in 1 ml of dry ACN under inert gas at 40° C. for 16 hrs. The product, comigrates with the starting material on TLC (5% isopropanol/CH$_2$Cl$_2$). The reaction was diluted with CH$_2$Cl$_2$ and washed with phosphate buffer, evaporated and purified on a preparative TLC plate eluting with 5% IsOH/CH$_2$Cl$_2$.

The recovered material was deprotected with 0.15M sodium hydroxide in dioxane/H$_2$O (1/1) at 20° C. for 16 hrs. The reaction was then neutralized with acetic acid, concentrated and purified by prep TLC eluting with H$_2$O/ACN (1/9). The product, 5' HO-T*-OCF$_2$O-T*-OH 3' had an Rf on silica TLC, eluting with H$_2$O/ACN (1/9), slightly faster than thymidine.

EXAMPLE 6

Preparation of a T-T Tetrahydropyran Ketal

5'-HO-3'-benzoyl thymidine was reacted with 5,6-dihydro-4-methoxy-2Hpyran producing 5'-(4-methoxy tetrahydro pyrano-4-yl) thymidine as described by Reese, C. B. et al., *Tetrahedron* (1970) 26:1023-1030. A mixture of 5'-piyaloyl thymidine 0.23 grams (0.5 mmol) and of the 5'-(4-methoxytetrahydropyran-4-yl)-3'-benzoyl thymidine (0.32 grams, 1 mmol) was rotovaped from dry acetonitrile (ACN) three times to render them anhydrous. This gum was then dissolved in 2 ml of dry ethanol-free chloroform (CHCl$_3$) and 1 gram of freshly activated 4A molecular sieves was added. The reaction was agitated on a shaker at 20° C. for 16 hrs under inert gas. 10 mmol of p-toluenesulfonic acid (TSA) (previously dried by evaporation three times from dry ACN) was added in 0.2 ml of dry CHCl$_3$ and the reaction was agitated for 2 hrs at 50° C. under inert gas. The reaction was cooled to 20° C. and quenched with 0.5 ml of triethylamine (TEA).

The workup consisted of dilution with CH$_2$Cl$_2$ and extraction with 0.5M sodium phosphate pH 9, rotovaping to dryness, dissolving in toluene and mixture was purified by preparative thin layer chromatography, eluting with 5% isopropanol in CH$_2$Cl$_2$.

I claim:

1. A modified oligonucleotide wherein said oligonucleotide contains a nucleotide sequence useful in binding a target substance, wherein the modification comprises substitution for one or more linkages between individual nucleoside residues of a linkage of the formula —YCX$_2$Y— wherein each Y is independently O or S and wherein each X is independently chosen and is selected from the group consisting of H; halo; alkyl (1-6C); carboxyl or an alkyl (1-6C) ester or alkyl (1-6C) amide thereof; —SOR or —SO$_2$R, wherein R is alkyl (1-6C); —CN; and —CF$_3$;

or wherein X is —(CH$_2$)$_{1-3}$W wherein W is selected from the group consisting of a primary, secondary, or tertiary amine hydroxymethyl, —OCH$_2$OCH$_2$OH, —OCH$_2$CH$_2$OH, —COOCH$_3$, —CONHCH$_2$CH$_3$, —COOH and CF$_3$, or wherein both X taken together with the C of CX$_2$ form a heterocyclic ring selected from the group consisting of and 2. The modified oligonucleotide of claim 1 wherein both X with respect to each —YCX$_2$Y— linkage are identical.

3. The modified oligonucleotide of claim 1 wherein at least two linkages are said —YCX$_2$Y— linkages.

4. The modified oligonucleotide of claim 1 wherein at least one —Y—CX$_2$Y— is —OCH$_2$O—, or —SCH$_2$O—.

5. The modified oligonucleotide of claim 4 wherein said —YCX$_2$Y— is —SCH$_2$O—.

6. The modified oligonucleotide of claim 1 which is a dimer or trimer.

7. The modified oligonucleotide of claim 1 wherein the —YCX$_2$Y— linkage is —OCX$_2$S—; —SCX$_2$O—; or —SCX$_2$S—.

8. An oligomer of the formula wherein said oligomer contains a nucleotide sequence useful in binding a target substance, wherein each B is independently a purine or pyrimidine moiety, and wherein each Z is independently

—P(O)O$^-$— or is

—CX$_2$—; and wherein each X is independently selected from the group consisting of H; halo; alkyl (1-6C); carboxyl or an alkyl (1-6C) ester or alkyl (1-6C) amide thereof; —SOR or —SO$_2$R, wherein R is alkyl (1-6C); —CN; and —CF$_3$;

or wherein X is —(CH$_2$)$_{1-3}$W wherein W is selected from the group consisting of a primary, secondary, or tertiary amine; hydroxymethyl, OCH$_2$OCH$_2$OH, —OCH$_2$CH$_2$OH, —COOCH$_3$, —CONHCH$_2$CH$_3$, —COOH and CF$_3$;

or wherein both X taken together with the C of CX$_2$ from a heterocyclic ring selected from the group consisting of and n is 1-200; each m is 0 or 1, and wherein at least one Z is CX$_2$, and wherein each Y is independently O or S.

9. The oligomer of claim 8 wherein both X with respect to each CX$_2$ are identical.

10. The oligomer of claim 8 wherein at least one —YCX$_2$Y— is —OCH$_2$O—, —OCF$_2$O—, the pyran ketal, or —SCH$_2$O—.

11. The oligomer of claim 8 wherein said —YCX$_2$Y— is —SCH$_2$O—.

12. The oligomer of claim 8 which is a dimer or trimer.

* * * * *